United States Patent
Dubois et al.

(10) Patent No.: US 7,161,028 B2
(45) Date of Patent: Jan. 9, 2007

(54) METHOD FOR PRODUCING ACRYLIC ACID FROM PROPANE IN THE ABSENCE OF MOLECULAR OXYGEN

(75) Inventors: Jean-Luc Dubois, Millery (FR); Stephanie Serreau, Oullins (FR); Julien Jacquel, Ham Sous Varsberg (FR)

(73) Assignee: Arkema France, Puteaux (FR)

( * ) Notice: Subject to any disclaimer, the term of this patent is extended or adjusted under 35 U.S.C. 154(b) by 416 days.

(21) Appl. No.: 10/497,210

(22) PCT Filed: Nov. 28, 2002

(86) PCT No.: PCT/FR02/04089

§ 371 (c)(1),
(2), (4) Date: Jun. 1, 2004

(87) PCT Pub. No.: WO03/045886

PCT Pub. Date: Jun. 5, 2003

(65) Prior Publication Data

US 2005/0054880 A1 Mar. 10, 2005

(30) Foreign Application Priority Data

Nov. 30, 2001 (FR) .................................. 01 15524

(51) Int. Cl.
*C07C 51/16* (2006.01)

(52) U.S. Cl. ...................................................... 562/549
(58) Field of Classification Search ..................... None
See application file for complete search history.

(56) References Cited

U.S. PATENT DOCUMENTS

| 4,341,717 A | 7/1982 | Callahan et al. |
| 5,380,933 A | 1/1995 | Ushikubo et al. |
| 6,281,384 B1 | 8/2001 | Contracter et al. |

FOREIGN PATENT DOCUMENTS

| EP | 0608838 | 8/1994 |
| WO | WO 0104079 | 1/2001 |

*Primary Examiner*—Paul A. Zucker

(57) ABSTRACT

The invention concerns a method for producing acrylic acid from propane in the absence of molecular oxygen. Said method is characterized in that it consists in passing a gas mixture free of molecular oxygen and comprising propane, water vapour, as well as, optionally, an inert gas, over a catalyst including molybdenum, vanadium, tellurium, oxygen and at least another element X selected among niobium, tantalum, tungsten, titanium, aluminium, zirconium, chromium, manganese, iron, ruthenium, cobalt, rhodium, nickel, palladium, platinum, antimony, bismuth, boron, indium and cerium, and on a co-catalyst of formula (II): $Mo_1Bi_aFe_bCo_cNi_dK_eSb_fTi_gSi_hCa_iNb_jTe_kPb_lW_mCu_n$.
The invention also concerns a solid catalytic composition comprising said catalyst and co-catalyst and the use of said composition for producing acrylic acid from propane.

16 Claims, No Drawings

METHOD FOR PRODUCING ACRYLIC ACID FROM PROPANE IN THE ABSENCE OF MOLECULAR OXYGEN

The present invention relates to the production of acrylic acid from propane in the absence of molecular oxygen.

European patent application No. 608 838 describes the preparation of an unsaturated carboxylic acid, such as acrylic acid, from an alkane such as propane, by subjecting this alkane to a reaction of vapour-phase catalytic oxidation optionally devoid of molecular oxygen and in the presence of a catalyst containing a mixed oxide of metals essentially comprising molybdenum, vanadium, tellurium, oxygen and at least one other element X selected from niobium, tantalum, tungsten, titanium, aluminium, zirconium, chromium, manganese, iron, ruthenium, cobalt, rhodium, nickel, palladium, platinum, antimony, bismuth, boron, indium and cerium, with the proportions of these elements satisfying the following conditions:

$$0.25 < r_{Mo} < 0.98$$

$$0.003 < r_V < 0.5$$

$$0.003 < r_{Te} < 0.5$$

$$0.003 < r_X < 0.5$$

in which $r_{Mo}$, $r_V$, $r_{Te}$ and $r_X$ represent, respectively, the molar fractions of Mo, V, Te and X, relative to the sum of the numbers of moles of all the elements of the catalyst, with the exception of oxygen.

A major drawback of this process is that propionic acid is produced as a by-product. This acid poses problems in certain applications of acrylic acid when it is present in excessive amounts.

The invention therefore has the aim of reducing the production of propionic acid in such a process.

Thus, the invention relates to a process such as has just been described but in which the gas mixture is in addition passed over a co-catalyst.

The invention therefore relates more precisely to a process for the manufacture of acrylic acid from propane, in which a gas mixture devoid of molecular oxygen and containing propane, steam, as well as, if necessary, an inert gas, is passed over a catalyst containing molybdenum, vanadium, tellurium, oxygen and at least one other element X selected from niobium, tantalum, tungsten, titanium, aluminium, zirconium, chromium, manganese, iron, ruthenium, cobalt, rhodium, nickel, palladium, platinum, antimony, bismuth, boron, indium and cerium, in order to oxidize the propane according to the following redox reaction (1):

$$\text{SOLID}_{oxidized} + \text{PROPANE} \rightarrow \text{SOLID}_{reduced} + \text{ACRYLIC ACID} \quad (1)$$

the said process being characterized in that the gas mixture is also passed over a co-catalyst of formula (II)

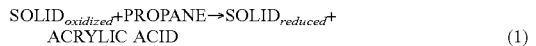
$$\text{Mo}_1\text{Bi}_{a'}\text{Fe}_{b'}\text{Co}_{c'}\text{Ni}_{d'}\text{K}_{e'}\text{Sb}_{f'}\text{Ti}_{g'}\text{Si}_{h'}\text{Ca}_{i'}\text{Nb}_{j'}\text{Te}_{k'}\text{Pb}_{l'}\text{W}_{m'}\text{Cu}_{n'}. \quad (II)$$

in which:
a' is comprised between 0.006 and 1, inclusive;
b' is comprised between 0 and 3.5, inclusive;
c' is comprised between 0 and 3.5, inclusive;
d' is comprised between 0 and 3.5, inclusive;
e' is comprised between 0 and 1, inclusive;
f' is comprised between 0 and 1, inclusive;
g' is comprised between 0 and 1, inclusive;
h' is comprised between 0 and 3.5, inclusive;
i' is comprised between 0 and 1, inclusive;
j' is comprised between 0 and 1, inclusive;
k' is comprised between 0 and 1, inclusive;
l' is comprised between 0 and 1, inclusive;
m' is comprised between 0 and 1, inclusive; and
n' is comprised between 0 and 1, inclusive.

Such a process therefore permits considerable reduction of the propionic acid/acrylic acid ratio at the reactor outlet.

In addition, it also reduces the formation of acetone, which is also a by-product in the manufacture of acrylic acid from propane.

The invention relates to a solid catalytic composition comprising:
a) the catalyst as defined above; as well as
b) the co-catalyst as defined above.

Other characteristics and advantages of the invention will now be described in detail in the following description.

DETAILED DESCRIPTION OF THE INVENTION

The co-catalyst used in the process according to the invention corresponds to formula (II) given above.

The oxides of the various metals included in the composition of the mixed oxide of formula (II) can be used as starting materials in the preparation of the said composition, but the starting materials are not limited to oxides; as other starting materials, there can be mentioned:
- in the case of molybdenum, ammonium molybdate, ammonium paramolybdate, ammonium heptamolybdate, molybdic acid, halides or oxyhalides of molybdenum such as $MoCl_5$, organometallic compounds of molybdenum such as molybdenum alkoxides such as $Mo(OC_2H_5)_5$, molybdenyl acetylacetone;
- in the case of vanadium, ammonium metavanadate, halides or oxyhalides of vanadium such as $VCl_4$, $VCl_5$ or $VOCl_3$, organometallic compounds of vanadium such as vanadium alkoxides such as $VO(OC_2H_5)_3$;
- in the case of niobium, niobic acid, $Nb_2(C_2O_4)_5$, niobium tartrate, niobium hydrogen oxalate, oxotrioxalatoammonium niobate $\{(NH_4)_3[NbO(C_2O_4)_3 \cdot 1.5H_2O]\}$, oxalate of niobium and ammonium, oxalate of niobium and tartrate, halides or oxyhalides of niobium such as $NbCl_3$, $NbCl_5$ and organometallic compounds of niobium such as niobium alkoxides such as $Nb(OC_2H_5)_5$, $Nb(O\text{-}n\text{-}Bu)_5$;
- in the case of nickel, cobalt, bismuth, iron or potassium, the corresponding nitrates;

and, in general, all the compounds that are able to form an oxide by calcination, namely, the metal salts of organic acids, the metal salts of mineral acids, metal complexes, etc.

The source of silicon generally consists of colloidal silica.

According to particular embodiments, solid compositions of formula (II) can be prepared by mixing, while stirring, aqueous solutions of niobic acid, ammonium heptamolybdate, ammonium metavanadate, and telluric acid, preferably adding colloidal silica, then precalcining in air at about 300° C. and calcining under nitrogen at about 600° C.

Preferably, in the co-catalyst of formula (II):
a' is comprised between 0.01 and 0.4, inclusive;
b' is comprised between 0.2 and 1.6, inclusive;
c' is comprised between 0.3 and 1.6, inclusive;
d' is comprised between 0.1 and 0.6, inclusive;
e' is comprised between 0.006 and 0.01, inclusive;
f' is comprised between 0 and 0.4, inclusive;

g' is comprised between 0 and 0.4, inclusive;
h' is comprised between 0.01 and 1.6, inclusive;
i' is comprised between 0 and 0.4, inclusive;
j' is comprised between 0 and 0.4, inclusive;
k' is comprised between 0 and 0.4, inclusive;
l' is comprised between 0 and 0.4, inclusive;
m' is comprised between 0 and 0.4, inclusive; and
n' is comprised between 0 and 0.4, inclusive.

According to one embodiment of the invention, the catalyst is as used in the process of European patent application No. 608 838 cited above, and in particular, the catalyst of formula $Mo_1V_{0.3}Te_{0.23}Nb_{0.12}O_n$, the preparation of which is described in Example 1 of that patent application.

According to a preferred embodiment of the invention, the catalyst corresponds to the following formula (I):

$$Mo_1V_aTe_bNb_cSi_dO_x \quad (I)$$

in which:
a is comprised between 0.006 and 1, inclusive;
b is comprised between 0.006 and 1, inclusive;
c is comprised between 0.006 and 1, inclusive;
d is comprised between 0 and 3.5, inclusive; and
x is the amount of oxygen bound to the other elements and depends on their oxidation states.

Advantageously:
a is comprised between 0.09 and 0.8, inclusive;
b is comprised between 0.04 and 0.6, inclusive;
c is comprised between 0.01 and 0.4, inclusive; and
d is comprised between 0.4 and 1.6, inclusive.

Such a catalyst can be prepared in the same way as the co-catalyst of formula (II) and from the same starting materials with, in addition, as a source of tellurium, tellurium oxide, telluric acid or, in general, all compounds that are able to form an oxide of tellurium by calcination, namely, the metal salts of organic acids, the metal salts of mineral acids, metal complexes, etc.

According to the invention, the manufacture of acrylic acid is carried out by passing a gas mixture devoid of molecular oxygen and containing propane and steam, as well as, if appropriate, an inert gas, over a catalyst and a co-catalyst as defined above, to effect the redox reaction (1) as shown above.

The mass ratio of catalyst to co-catalyst is generally greater than 0.5 and preferably at least 1.

According to an advantageous embodiment of the invention, the catalyst and the co-catalyst are situated in the same reactor. Thus, the redox reaction is implemented in just one stage.

The catalyst and the co-catalyst can be in the form of a solid catalytic composition.

They can each be in the form of granules, the catalyst and co-catalyst pellets being mixed before applying the process according to the invention.

The catalyst and the co-catalyst can also be in the form of a solid catalytic composition consisting of pellets each one of which contains both the catalyst and the co-catalyst.

Generally, redox reaction (1) is carried out at a temperature from 200 to 500° C., preferably from 250 to 450° C., even more preferably from 350 to 400° C.

The pressure is generally from $1.01 \times 10^4$ to $1.01 \times 10^6$ Pa (0.1 to 10 atmospheres), preferably from $5.05 \times 10^4$ to $5.05 \times 10^5$ Pa (0.5–5 atmospheres).

Residence time is generally from 0.01 to 90 seconds, and preferably from 0.1 to 30 seconds.

The propane/steam ratio by volume in the gas phase is not critical and can vary over a wide range.

Similarly, the proportion of inert gas, which can be helium, krypton, a mixture of these two gases, or alternatively nitrogen, carbon dioxide, etc., is not critical either and can also vary over a wide range.

As the order of magnitude of the proportions of the starting mixture, there can be mentioned the following ratio (by volume):

propane/inert (He—Kr) /$H_2O$ (steam): 10–20/40–50/40–50

In the course of redox reaction (1), the solid composition undergoes reduction and, in general, a progressive loss of its activity. That is why, once the solid composition has been converted at least partially to the reduced state, regeneration of the said solid composition is carried out according to reaction (2):

$$SOLID_{reduced} + O_2 \rightarrow SOLID_{oxidized} \quad (2)$$

by heating in the presence of oxygen or a gas containing oxygen at a temperature from 250 to 500° C., for the time necessary for reoxidation of the solid composition.

In general the process is applied until the degree of reduction of the solid composition is comprised between 10 and 40%.

The said degree of reduction can be monitored during the reaction from the quantity of products obtained. Then the equivalent quantity of oxygen is calculated. The said monitoring can also be based on the exothermic character of the reaction.

After regeneration, which can be carried out under temperature and pressure conditions that are identical to or different from those of the redox reaction, the solid composition regains its initial activity and can be used in a new reaction cycle.

Redox reaction (1) and the regeneration can be carried out in a conventional reactor, such as a fixed-bed reactor, a fluidized-bed reactor or a transport-bed reactor.

It is therefore possible to carry out redox reaction (1) and regeneration in a two-stage device, i.e. a reactor and a regenerator which operate simultaneously and in which two batches of solid composition alternate periodically; it is also possible to carry out redox reaction (1) and regeneration in one and the same reactor, alternating the periods of reaction and regeneration.

Preferably, redox reaction (1) and regeneration are carried out in a reactor with a transport bed of catalyst.

It is possible to use a single-pass operating mode or an operating mode with recycling.

According to a preferred embodiment, the propylene produced as by-product and/or the unreacted propane are recycled (or returned) to the reactor inlet, i.e. they are reintroduced at the reactor inlet, mixed with or parallel with the starting mixture of propane, steam and, if necessary, inert gas(es).

EXAMPLES

The following examples illustrate the present invention without however limiting its scope.

In the formulae given in Examples 1 to 3, x is the amount of oxygen bound to the other elements and depends on their oxidation states.

The selectivities and yields are defined as follows:

$$\text{Selectivity (\%) with respect to acrylic acid} = \frac{\text{Number of moles of acrylic acid formed}}{\text{Number of moles of propane that reacted}} \times 100$$

$$\text{Yield (\%) with respect to acrylic acid} = \frac{\text{Number of moles of acrylic acid formed}}{\text{Number of moles of propane introduced}} \times 100$$

The selectivities and yields relative to the other compounds are calculated similarly.

Example 1

Preparation of Catalyst A of Formula $Mo_1V_{0.33}Nb_{0.11}Te_{0.22}Si_{0.95}O_x$ a) Preparation of a Solution of Niobium 640 g of distilled water then 51.2 g of niobic acid (i.e. 0.304 moles of niobium) are introduced into a 5-liter beaker. Then 103.2 g (0.816 mol) of oxalic acid dihydrate is added.

The oxalic acid/niobium molar ratio is therefore 2.69.

The solution obtained previously is heated at 60° C. for 2 hours, with covering to prevent evaporation, and stirring. A white suspension is obtained, which is left to cool down, while stirring, to 30° C., which takes about 2 hours.

b) Preparation of a solution of Mo, V and Te 2120 g of distilled water, 488 g of ammonium heptamolybdate (i.e. 2.768 mol of molybdenum), 106.4 g of ammonium metavanadate $NH_4VO_3$ (i.e. 0.912 mol of vanadium) and 139.2 g of telluric acid (supplier: FLUKA) (i.e. 0.608 mol of tellurium) are introduced into a 5-liter beaker.

The solution obtained previously is heated at 60° C. for 1 hour 20 minutes, with covering to prevent evaporation, and stirring. A clear red solution is obtained, which is left to cool down, while stirring, to 30° C., which takes about 2 hours.

c) Introduction of the Silica 393.6 g of Ludox silica (containing 40% by weight of silica, supplied by the company Dupont) is introduced while stirring, into the solution of Mo, V and Te prepared previously. The latter remains clear and still has a red colouration.

Then, the solution of niobium prepared previously is added. A fluorescent orange gel is obtained after stirring for some minutes. This solution is then dried by atomization. The atomizer used is a laboratory atomizer (ATSELAB from the company Sodeva). Atomization takes place under a nitrogen atmosphere (in order to prevent any oxidation and any premature combustion of the oxalic acid present in the slurry).

The operating parameters are, overall:
nitrogen flow rate of the order of 45 $Nm^3/h$;
flow rate of slurry of the order of 500 g/h;
inlet temperature of the gases comprised between 155° C. and 170° C.;
outlet temperature of the gases comprised between 92° C. and 100° C.

Then the product recovered (355.2 g), which has a grain size of less than 40 microns, is placed in an oven at 130° C. overnight, in a PTFE-coated pan.

331 g of dry product is obtained.

d) Calcination

The precalcinations and calcinations were carried out under a stream of air and nitrogen in steel vessels. The said vessels are placed directly in muffle furnaces and the air is supplied via the flue. An internal thermometer well permits precise monitoring of temperature. The cover can be used to prevent air returning to the catalyst.

Firstly, the 331 g of the precursor obtained previously is precalcined for 4 hours at 300° C. under air flow of 47.9 ml/min/g of precursor.

The solid obtained is then calcined for 2 hours at 600° C. under a nitrogen flow of 12.8 ml/min/g of solid.

Catalyst A is thus obtained.

Example 2

Preparation of Co-catalyst B of Formula $Mo_1Bi_{0.08}Fe_{0.31}Co_{0.39}Ni_{0.22}K_{0.008}Sb_{0.08}Si_{0.66}O_x$ A solution A is prepared by dissolving 79.7 g of ammonium heptamolybdate in 220.3 g of water at ambient temperature, while stirring, for 5 minutes.

A colourless solution A is thus obtained.

A solution B is prepared by dissolving 51.5 g of cobalt nitrate and 0.3327 g of potassium nitrate in 55 g of water at ambient temperature, while stirring, for 5 minutes.

A purple solution B is thus obtained.

A solution C is prepared by dissolving 56.4 g of iron nitrate, 19.3 g of bismuth nitrate and 28.6 g of nickel nitrate in 85.1 g of water, in the following way: the nitrates are introduced into a small quantity of water, 4.4 g of 68% nitric acid is added, then the rest of the water is added. Stirring is carried out for 30 to 45 minutes.

A green solution C is thus obtained.

A solution D is prepared by dissolving 44.5 g of silica LUDOX AS40 in 16.4 g of distilled water at ambient temperature, while stirring.

A solution D is thus obtained.

Next, solution B is poured into solution A and stirring is carried out for 10 minutes. Then 5.9 g of antimony trioxide and solution C are added over 10 minutes.

Finally, solution D is added over 10 minutes followed by 16.2 g of ammonia (at 28% by weight) to adjust the pH of the solution to 2.3.

While still stirring, the temperature is raised to 70° C. and the reaction medium is maintained at this temperature for 90 minutes.

Then vacuum evaporation is carried out using a water bath and with stirring, until a thick gel is obtained. Drying of the precursor is then completed in the oven at 130° C. for 24 hours. 158.3 g of dry precursor is thus recovered. Calcination is carried out under air (47 ml/min/g of precursor) according to the following programme:
temperature rise of 2° C./min to 320° C.;
plateau at 320° C. for 2 hours;
temperature rise of 2° C./min to 540° C.;
plateau at 540° C. for 999 minutes (16.7 hours).

23.9 g of co-catalyst B is thus obtained.

Example 3

Preparation of Co-catalyst C of Formula $Mo_1Bi_{0.08}Fe_{0.31}CO_{0.39}Ni_{0.22}K_{0.008}Ti_{0.04}Si_{0.08}O_x$ a) Preparation of the Precursor A solution of 7970.0 g of ammonium heptamolybdate in 22000 g of distilled water is added, in a mixer, to a solution of 5151 g of cobalt nitrate hexahydrate and 33.0 g of potassium nitrate in 5000 g of water. The resulting solution is stirred for 10 minutes at ambient temperature, followed by pouring into 127.6 g of $TiO_2$ with a grain size less than 1 micron. Then a solution consisting of:

5637 g of unhydrated ferric nitrate,
1920 g of bismuth nitrate pentahydrate,
2859 g of nickel nitrate hexahydrate,
417 g of 68% nitric acid and
8500 g of distilled water, is added over 10 minutes.

Finally 594 g of a solution of colloidal silica at 30% by weight of silica in 1500 g of distilled water is added over 5 minutes.

The mixture is maintained under stirring at ambient temperature. Then, the temperature is raised progressively to 70° C. The mixture is maintained under stirring at this temperature for 90 minutes. Then the heating and stirring are turned off and the mixture is left to cool down to ambient temperature. The mixture contains about 33% by weight of solids and its pH is below 1. The mixture is then micronized in a ball mill until particles are obtained with an average size of less than 2 microns.

b) Preparation of a Solution of Polysilicic Acid (PSA) at 6% by Weight of Silica This solution is prepared by diluting 1091 g of a solution of sodium silicate (360 g of silica) with 4909 g of distilled water. The solution is mixed for some minutes; the pH of the mixture is about 12. Next, a sulphonic cation exchange resin marketed by the company Dow Chemicals under the trademark DOWEX Monosphere 650C (H) is added while stirring vigorously, until the pH of the mixture is comprised between 2.5 and 3. Then, the resin is filtered and the filtrate is stored in ice and must be used within the next hour for preparing a suspension of precursor-solution of PSA for atomization.

c) Preparation and Atomization of the Suspension of Precursor-Solution of PSA 1110 g of the solution of PSA at 6% silica (obtained in the preceding stage) is added to 2000 g of the micronized precursor mixture and the whole is maintained under stirring in ice. The resulting suspension, which contains 22.7% of solids, has a pH of 1±0.1. This suspension is atomized at a rate of about 200 ml/min, with a nozzle pressure of 0.3 bar and a chamber temperature of 390° C., so as to obtain porous microspheres, which can be used in the transport-bed redox process.

d) Calcination

The microspheres collected under the atomizer chamber are calcined in a furnace by heating from ambient temperature to 90° C. over 1 hour, holding the temperature at 90° C. for 2 hours, then heating to 300° C. over 2 hours, and holding the temperature at 300° C. for 5 hours, then heating to 550° C. over 2 hours and holding the temperature at 550° C. for 6 hours.

The desired co-catalyst C is thus obtained.

Example 4 a) Operating Method

The operating method adopted is described in detail below.

A vertical reactor is charged, from bottom to top, with a first depth of 1 ml of silicon carbide in the form of particles with a diameter of 0.62 mm, a second depth of 1 ml of silicon carbide in the form of particles with a diameter of 0.125 mm and 5 g of catalyst in the form of particles from 0.02 to 1 mm, then a third depth of silicon carbide in the form of particles with a diameter of 1.19 mm.

Then the reactor is heated to 250° C. and the vaporizer is heated to 200° C. The electric water pump is turned on.

Once the reactor and the vaporizer have reached the temperatures stated above, the water pump is started and the temperature of the reactor is raised to 380° C., followed by waiting for 30 minutes for the hot point to stabilize.

Then, oxygen is introduced in 10 bursts of 23 seconds each for thorough oxidation of the catalyst. The catalyst is considered to be completely oxidized when the temperature of the hot point has stabilized, i.e. when there is no longer evolution of heat due to the reaction (by monitoring the temperature of the catalyst, measured by means of a thermocouple placed in the catalyst bed, it is possible to see the temperature fluctuations in relation to the bursts).

With regard to acrylic acid production proper, a redox assay is made up of 60 redox cycles. A redox cycle represents:

9.5 or 12 seconds of propane, as necessary, in a continuous flow of helium-krypton/water,
45 seconds of continuous flow of helium-krypton/water,
20 seconds of oxygen in a continuous flow of helium-krypton/water,
45 seconds of continuous flow of helium-krypton/water.

During the assay, four samples of liquid are taken, each representing 15 cycles. Four samples of gas are also taken by means of gas bags, each sample representing about 15 cycles.

Each small wash bottle (of 25 ml capacity, and filled with 20 ml of water) is equipped with a gas bag, and when the bottle is connected to the reactor outlet (once the liquid forms bubbles), the bag is opened and the stopwatch is started.

To check the oxidation state of the catalyst, a new series of 10 bursts of 23 seconds of oxygen is carried out. It shows that the oxidation state of the solid was maintained during the assay.

The liquid effluents are analysed on a type HP 6890 chromatograph, after specific calibration has been carried out.

The gases are analysed during the assay on a micro-GC Chrompack chromatograph.

An acidity determination is carried out on each bottle in order to determine the exact number of moles of acid produced in the course of each micro-assay and to validate the chromatographic analyses.

The final result that is reported corresponds to the average of the micro-assays effected on the 4 wash bottles and the 4 gas bags.

b) Results b1) Tests T1 and T2

A first test T1 was carried out with 5 g of catalyst A. The duration of the propane bursts had been adjusted to about 9.5 s, by controlling the opening time of the mass flowmeter. The number of moles of propane sent onto the catalyst is thus predetermined. The operating method described above is followed. The results obtained are presented in Table 1.

A second test T2 was carried out, but instead of charging the reactor with 5 g of catalyst A it was charged with a mechanical mixture of 5 g of catalyst A and 5 g of co-catalyst B. The operating parameters were identical. The results obtained are shown in Table 1 below.

| Test | T1 | | T2 | |
|---|---|---|---|---|
| Catalyst | 5 g of A | | 5 g of A | |
| Co-catalyst | — | | 5 g of B | |
| Pressure drop (bar) | 0.18 | | 0.40 | |
| Duration of bursts (s) | 9.5 | | 9.5 | |
| | Yield (%) | Selectivity (%) | Yield (%) | Selectivity (%) |
| Acrylic acid | 10.5 | 59.6 | 10.5 | 49.3 |
| Acetic acid | 1.05 | 5.96 | 1.39 | 6.54 |
| Acrolein | 0.00 | 0.00 | 0.07 | 0.31 |
| Acetone | 0.17 | 0.98 | 0.06 | 0.29 |
| Propionic acid | 0.08 | 0.45 | 0.02 | 0.10 |
| Allyl alcohol | 0.00 | 0.00 | 0.00 | 0.00 |
| Allyl acrylate | 0.00 | 0.00 | 0.00 | 0.00 |
| Propanaldehyde | 0.00 | 0.00 | 0.00 | 0.00 |
| Acetaldehyde | 0.00 | 0.00 | 0.00 | 0.00 |
| CO | 1.37 | 7.78 | 3.46 | 16.3 |
| $CO_2$ | 1.27 | 7.22 | 3.59 | 16.9 |
| Propylene | 3.17 | 18.0 | 2.20 | 10.3 |
| Propane | 77.1 | | 73.8 | |
| Carbon balance (%) | 94.7 | | 95.1 | |
| Propionic acid/acrylic acid ratio | | 0.75% | | 0.20% |
| Acetone/acrylic acid ratio | | 1.64% | | 0.59% |

It can therefore be seen that adding the co-catalyst makes it possible to lower the propionic acid/acrylic acid ratio from 0.75% to 0.20%.

In addition, the acetone/acrylic acid ratio drops from 1.64% to 0.59%.

b2) Tests T3 and T4

A third test T3 was carried out with 5 g of catalyst A. The duration of the propane bursts had been adjusted to about 12 s, by controlling the opening time of the mass flowmeter. The number of moles of propane sent onto the catalyst is thus predetermined. The operating method described above is followed. The results obtained are presented in Table 2.

A fourth test T4 was carried out, but instead of charging the reactor with 5 g of catalyst A it was charged with a mechanical mixture of 5 g of catalyst A and 5 g of co-catalyst C. The operating parameters were identical. The results obtained are shown in Table 2 below.

| Test | T3 | | T4 | |
|---|---|---|---|---|
| Catalyst | 5 g of A | | 5 g of A | |
| Co-catalyst | — | | 5 g of C | |
| Pressure drop (bar) | 0.25 | | 0.35 | |
| Duration of bursts (s) | 12 | | 12 | |
| | Yield (%) | Selectivity (%) | Yield (%) | Selectivity (%) |
| Acrylic acid | 10.7 | 51.4 | 11.3 | 45.0 |
| Acetic acid | 0.99 | 4.73 | 1.16 | 4.62 |
| Acrolein | 0.09 | 0.42 | 0.02 | 0.09 |
| Acetone | 0.12 | 0.56 | 0.04 | 0.17 |
| Propionic acid | 0.04 | 0.18 | 0.01 | 0.04 |
| Allyl alcohol | 0.00 | 0.00 | 0.00 | 0.00 |
| Allyl acrylate | 0.00 | 0.00 | 0.00 | 0.00 |
| Propanaldehyde | 0.00 | 0.00 | 0.00 | 0.00 |
| Acetaldehyde | 0.00 | 0.00 | 0.00 | 0.00 |
| CO | 3.15 | 15.1 | 5.78 | 22.9 |
| $CO_2$ | 2.67 | 12.8 | 5.30 | 21.0 |
| Propylene | 3.09 | 14.8 | 1.55 | 6.15 |
| Propane | 76.5 | | 72.4 | |
| Carbon balance (%) | 97.3 | | 97.6 | |
| Propionic acid/acrylic acid ratio | | 0.35% | | 0.09% |
| Acetone/acrylic acid ratio | | 1.09% | | 0.38% |

It can therefore be seen that adding the co-catalyst makes it possible to lower the propionic acid/acrylic acid ratio from 0.35% to 0.09%.

In addition, the acetone/acrylic acid ratio drops from 1.09% to 0.38%.

The invention claimed is:

1. Process for the manufacture of acrylic acid from propane, in which a gas mixture devoid of molecular oxygen and containing propane, steam, as well as, if appropriate, an inert gas, is passed over a catalyst containing molybdenum, vanadium, tellurium, oxygen and at least one other element X selected from niobium, tantalum, tungsten, titanium, aluminium, zirconium, chromium, manganese, iron, ruthenium, cobalt, rhodium, nickel, palladium, platinum, antimony, bismuth, boron, indium and cerium, in order to oxidize the propane according to the following redox reaction (1):

$$SOLID_{oxidized} + PROPANE * SOLID_{reduced} + ACRYLIC\ ACID \qquad (1)$$

this process being characterized in that the gas mixture is also passed over a co-catalyst of formula (II)

  (II)

in which:

a' is comprised between 0.006 and 1, inclusive;
b' is comprised between 0 and 3.5, inclusive;
c' is comprised between 0 and 3.5, inclusive;
d' is comprised between 0 and 3.5, inclusive;
e' is comprised between 0 and 1, inclusive;
f' is comprised between 0 and 1, inclusive;
g' is comprised between 0 and 1, inclusive;
h' is comprised between 0 and 3.5, inclusive;
i' is comprised between 0 and 1, inclusive;
j' is comprised between 0 and 1, inclusive;
k' is comprised between 0 and 1, inclusive;
l' is comprised between 0 and 1, inclusive;
m' is comprised between 0 and 1, inclusive; and
n' is comprised between 0 and 1, inclusive.

2. Process according to claim 1, in which, in the co-catalyst of formula (II):

a' is comprised between 0.01 and 0.4, inclusive;
b' is comprised between 0.2 and 1.6, inclusive;
c' is comprised between 0.3 and 1.6, inclusive;
d' is comprised between 0.1 and 0.6, inclusive;
e' is comprised between 0.006 and 0.01, inclusive;
f' is comprised between 0 and 0.4, inclusive;
g' is comprised between 0 and 0.4, inclusive;
h' is comprised between 0.01 and 1.6, inclusive;
i' is comprised between 0 and 0.4, inclusive;
j' is comprised between 0 and 0.4, inclusive;
k' is comprised between 0 and 0.4, inclusive;
l' is comprised between 0 and 0.4, inclusive;

m' is comprised between 0 and 0.4, inclusive; and
n' is comprised between 0 and 0.4, inclusive.

3. Process according to claim 1, in which the proportions of the elements of the catalyst satisfy the following conditions:

$$0.25 < r_{Mo} < 0.98$$

$$0.003 < r_V < 0.5$$

$$0.003 < r_{Te} < 0.5$$

$$0.003 < r_X < 0.5$$

in which $r_{Mo}$, $r_V$, $r_{Te}$ and $r_X$ represent the molar fractions, respectively, of Mo, V, Te and X, relative to the sum of the numbers of moles of all of the elements of the catalyst, with the exception of oxygen.

4. Process according to claim 1, in which the catalyst corresponds to the following formula (I):

$$Mo_1V_aTe_bNb_cSi_dO_x \quad (I)$$

in which:
a is comprised between 0.006 and 1, inclusive;
b is comprised between 0.006 and 1, inclusive;
c is comprised between 0.006 and 1, inclusive;
d is comprised between 0 and 3.5, inclusive; and
x is the amount of oxygen bound to the other elements and depends on their oxidation states.

5. Process according to claim 4, in which, in formula (I):
a is comprised between 0.09 and 0.8, inclusive;
b is comprised between 0.04 and 0.6, inclusive;
c is comprised between 0.01 and 0.4, inclusive; and
d is comprised between 0.4 and 1.6, inclusive.

6. Process according to claim 1, in which a weight ratio of the catalyst to the co-catalyst greater than 0.5 and preferably of at least 1 is used.

7. Process according to claim 1, in which the catalyst and the co-catalyst are mixed together.

8. Process according to claim 1, in which the catalyst and the co-catalyst are in the form of pellets, with each pellet containing both the catalyst and the co-catalyst.

9. Process according to claim 1, in which redox reaction (1) is carried out at a temperature from 200 to 500° C. and preferably from 250 to 450° C.

10. Process according to claim 1, in which redox reaction (1) is carried out at a pressure from $1.01 \times 10^4$ to $1.01 \times 10^6$ Pa (0.1 to 10 atmospheres) and preferably from $5.05 \times 10^4$ to $5.05 \times 10^5$ Pa (0.5–5 atmospheres).

11. Process according to claim 1, in which redox reaction (1) is carried out with a residence time from 0.01 to 90 seconds and preferably from 0.1 to 30 seconds.

12. Process according to claim 1, characterized in that once the solid composition has been converted at least partially to the reduced state, regeneration of the said solid composition is carried out according to reaction (2):

$$SOLID_{reduced} + O_2 > SOLID_{oxidized} \quad (2)$$

by heating in the presence of oxygen or a gas containing oxygen at a temperature from 250 to 500° C., for the time required for reoxidation of the solid composition.

13. Process according to the preceding claim, characterized in that redox reaction (1) and regeneration are carried out in a two-stage device, namely a reactor and a regenerator which operate simultaneously and in which two batches of solid composition alternate periodically.

14. Process according to claim 12, characterized in that redox reaction (1) and regeneration are carried out in one and the same reactor by alternating the periods of reaction and regeneration.

15. Process according to claim 12, characterized in that redox reaction (1) and regeneration are carried out in a transport bed reactor.

16. Process according to claim 1, characterized in that the propylene produced and/or the unreacted propane are recycled to the reactor inlet.

* * * * *